United States Patent
Büttner et al.

[11] 3,983,172
[45] Sept. 28, 1976

[54] BIS-HALOGEN CARBONYL ANILINES AND PROCESS FOR THE PRODUCTION

[75] Inventors: Gerhard Büttner, Cologne; Erich Klauke, Odenthal-Hahnenberg; Klaus Sasse, Schildgen, all of Germany

[73] Assignee: Bayer Aktiengesellschaft, Leverkusen, Germany

[22] Filed: Mar. 1, 1974

[21] Appl. No.: 447,438

[30] Foreign Application Priority Data
Mar. 9, 1973 Germany............................ 2311662

[52] U.S. Cl................................ 260/544 C; 71/93;
260/248 NS; 260/465 D; 260/471 R
[51] Int. Cl.².............. C07C 125/00; C07C 125/03
[58] Field of Search.......... 260/544 N, 471 R, 465 D

[56] References Cited
UNITED STATES PATENTS

| | | |
|---|---|---|
| 3,457,294 | 7/1969 | Crovetti et al................ 260/544 N |
| 3,649,664 | 3/1972 | Richter et al................. 260/544 N |

FOREIGN PATENTS OR APPLICATIONS
1,517,379  3/1968  France

OTHER PUBLICATIONS
Fawcett et al., J. Am. Chem. Soc., 84 4275 (1962).

Primary Examiner—Richard L. Raymond
Attorney, Agent, or Firm—Burgess, Dinklage & Sprung

[57] ABSTRACT

Bis-halogen carbonyl anilines useful in the production of herbicides having the formula

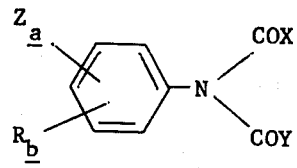

wherein
X is fluorine or chlorine,
Y is fluorine, chlorine, fluorocarbonyl, or chlorocarbonyl,
Z is halogen, nitro, cyano, lower alkyl sulfonyl or carbalkoxy,
R is lower alkyl, alkoxy, thioalkyl, phenyl, naphthyl, lower perhalogen alkyl, perhalogen alkoxy or perhalogen alkylthio,
$a$ and $b$ represent a number from 0 to 5, with the proviso that $a$ plus $b$ is at the most 5,
are prepared by reacting an aryl carbamic acid fluoride having the formula

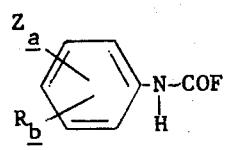

wherein
Z, R, $a$, $b$ are as defined above with an acylating agent having the formula

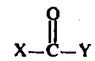

wherein
X and Y are as defined above in the presence of a tertiary amine at a temperature in the range of from −20° to +40°C.

8 Claims, No Drawings

BIS-HALOGEN CARBONYL ANILINES AND PROCESS FOR THE PRODUCTION

This invention relates to a new process for the production of bis-halogen carbonyl anilines, and to the new compounds with two different halogen atoms.

SUMMARY

It has been found that bis-halogen carbonyl anilines corresponding to the formula

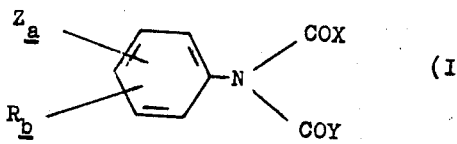

in which
X represents fluorine or chlorine;
Y represents fluorine, chlorine, the fluorcarbonyl radical or the chlorocarbonyl radical;
Z represents halogen, nitro, cyano, a lower alkyl sulphonyl or the carbalkoxy radical;
R represents a lower alkyl, alkoxy, thioalkyl radical, phenyl, naphthyl, and lower perhalogen alkyl, perhalogen alkoxy or perhalogen alkylthio;
$a$ and $b$ represent a number of from 0 to 5, $a$ plus $b$ being at most 5,
can be obtained by reacting arylcarbamic acid fluorides corresponding to the general formula (II)

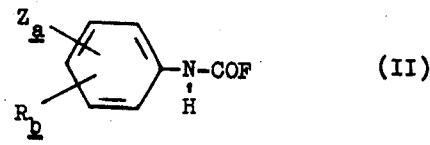

in which Z, R, $a$, $b$ are as just defined, with acylating agents corresponding to the general formula (III)

in which
X and Y are as defined above, in the presence of tertiary amines at temperatures of from —20 to +40°C.

DESCRIPTION

In the context of the present invention, "lower" alkyl radicals are alkyl radicals having from 1 to 6 and preferably having 1 to 4 carbon atoms. Preferred starting compounds (II) are those in which $a + b = 1$ to 3, more especially 1 or 2.

The compounds of general formula I are new where X and Y do not simultaneously represent fluorine or chlorine.

It must be regarded as extremely surprising that it is virtually only acylation of the aryl carbamic acid fluorides which takes place in the process according to the invention. It had been expected from the prior art (Annalen 562, page 78 (1949) that carbamic acid fluorides would react to form solely the corresponding isocyanates in the presence of tertiary amines.

The process according to the invention is illustrated with reference to the following example:

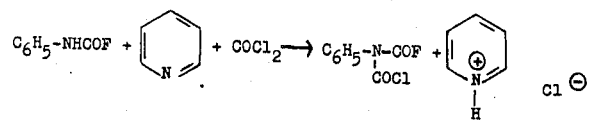

The aryl carbamic acid fluorides used as starting materials correspond to general formula (II). In this formula, R preferably represents optionally branched alkyl or alkoxy radicals having from 1 to 4 carbon atoms which can be substituted by halogen atoms (preferably chlorine and/or fluorine). In addition, R repesents the thioalkyl radical, preferably the thiomethyl radical, and also preferably the trifluoromethyl, trifluoromethoxy or the trifluoromethylthio radical. In the last three radicals, some of the fluorine can even be substituted by chlorine.

These starting materials are known compounds (Journal Chem. Soc. 1945, page 864) and can be obtained by known methods. The arylisocyanates required as preliminary stages for their production are also known (Liebigs Annalen der Chemie 562, pages 115 to 120; DAS 1,138,391).

The following are mentioned as examples of starting materials corresponding to formula II (with melting points in °C):
phenylcarbamic acid fluoride (32 – 34),
p-tolylcarbamic acid fluoride (56 – 57),
2,4-dimethyl phenyl carbamic acid fluoride (65 – 68),
2,4,5-trimethyl phenyl carbamic acid fluoride (77 – 80),
3,4,6-trichlorophenyl carbamic acid fluoride (103 – 105),
3,4-dichlorophenyl carbamic acid fluoride (92),
3-nitrophenyl carbamic acid fluoride (100),
2-chlorophenyl carbamic acid fluoride (114),
2,3-dichlorophenyl carbamic acid fluoride (80 – 85),
m-cyanophenyl carbamic acid fluoride (109 – 114),
3-chloromethylphenyl carbamic acid fluoride (67 – 70),
3-methoxyphenyl carbamic acid fluoride (61 – 64),
2,4-dimethyl-4-nitrophenyl carbamic acid fluoride (130 – 133),
4-ethoxyphenyl carbamic acid fluoride (60 – 63),
4-methylsulphonylphenyl carbamic acid fluoride (decomposition),
diphenylmethane-4-carbamic acid fluoride (85 – 88),
2-trifluoromethyl carbamic acid fluoride (40),
3,5-bis-trifluoromethylphenyl carbamic acid fluoride (55–58),
3-trifluoromethyl-5-bromophenyl carbamic acid fluoride (75–77).

The following represent particularly preferred aryl carbamic acid fluorides:
4-trifluoromethyl carbamic acid fluoride (83 – 85),
3-trifluoromethyl carbamic acid fluoride (73 – 74),
2-trifluoromethyl-4-chlorophenyl carbamic acid fluoride (58 – 61),
3-chloro-4-trifluoromethylphenyl carbamic acid fluoride (77– 82),
3-trifluoromethyl-4-methylphenyl carbamic acid fluoride (70 – 73), 3-chloro-4-fluorophenyl carbamic acid fluoride (65 – 69), 3-trifluoromethyl-4-chlorophenyl carbamic acid fluoride (93 – 94),
3-chloro-4-trifluoromethoxyphenyl carbamic acid fluoride (71 – 73),
3-chloro-4-methylphenyl carbamic acid fluoride (67 – 69),
3-chloro-4-thiomethylphenyl carbamic acid fluoride (67 – 71),
4-methoxy-5-chlorophenyl carbamic acid fluoride (73 – 75), Chlorocarbonic acid derivatives, such as difluoro phosgene and chlorofluoro phosgene, are mentioned as acylating agents of general formula (III), although phosgene and oxalyl chloride are preferably used. The acylating agent is used in a quantity of from 1 to 1.5 mols and preferably in a quantity of 1 to 1.2 mols per mol of carbamic acid fluoride (II).

The process according to the invention is generally carried out in the presence of inert organic solvents as diluents. Examples of suitable inert organic solvents include hydrocarbons such as benzene, toluene, xylene, chlorinated hydrocarbons, such as methylene chloride, tetrachlorethylene, chlorobenzene, dichlorobenzene, and ethers such as diethylether, dioxan and tetrahydrofuran.

The process according to the invention is carried out in the presence of tertiary amines as hydrogen chloride acceptors. In cases where alkylamines are used, the stoichiometrically necessary quantity of the base (calculated on carbamic acid fluoride) is used. In cases where aromatic tertiary amines are used, it is also possible to use an excess of from 0.1 to 0.2 mol of base. Exemplary representatives of tertiary amines are triethylamine, dimethylbenzylamine, dimethylaniline, pyridine, picoline, collidine, quinoline, pyrrolidine, preferably pyridine or 4-dimethylamino pyridine.

The process according to the invention is carried out at a temperature in the range of from −20 to +40°C, preferably at a temperature of from −15 to +30°C and more particularly at a temperature of from −10 to +10°C.

To carry out the process according to the invention, for example, 1 mol of aryl carbamic acid fluoride is dissolved in toluene or in chlorobenzene; from 1.0 to 1.1 mols of pyridine are slowly added dropwise with stirring at −15 to +30°C and 1.0 to 1.2 mols of phosgene are then introduced into the clear solution at the same temperature. After the phosgene has been introduced, the reaction mixture is allowed to come slowly to room temperature while stirring, the precipitate is filtered off under suction and the solvent removed under reduced pressure. The residue left is optionally washed with petrol or recrystallised.

The following represent preferred new compounds which can be obtained by the process according to the invention:
phenyl-N(chlorocarbonyl-fluorocarbonyl)-aniline;
3-chloro-4-methoxy-N(chlorocarbonyl-fluorocarbonyl)-aniline;
4-trifluoromethyl-N(chlorocarbonyl-fluorocarbonyl)-aniline;
3-trifluoromethyl-N(chlorocarbonyl-fluorocarbonyl)-aniline;
3-trifluoromethyl-4-chloro-N(chlorocarbonyl-fluorocarbonyl)-aniline;
3-chloro-4-trifluoromethoxy-N(chlorocarbonyl-fluorocarbonyl)-aniline;
3-chloro-4-methyl-N(chlorocarbonyl-fluorocarbonyl)-aniline;
3-chloro-4-thiomethyl-N(chlorocarbonyl-fluorocarbonyl)-aniline;
3-chloro-4-fluoro-N(chlorocarbonyl-fluorocarbonyl)-aniline;
3-cyano-N(chlorocarbonyl-fluorocarbonyl)-aniline;
4-methylsulphonyl-N(chlorocarbonyl-fluorocarbonyl)-aniline;
4-methyl-N(chlorocarbonyl-fluorocarbonyl)-aniline;
4-chloro-N(chlorocarbonyl-fluorocarbonyl)-aniline;
3,4-dichloro-N(chlorocarbonyl-fluorocarbonyl)-aniline and
3-nitro-N(chlorocarbonyl-fluorocarbonyl)-aniline.

The compounds which can be obtained by the process according to the invention can be used for the production of herbicides (German Patent Application P 2 254 200).

If the N(fluorocarbonyl-chlorocarbonyl)-anilines obtained by the process according to the invention are reacted with acetone-S-methylisothiosemicarbazone hydriodide in the presence of triethylamine, followed by splitting in weakly acid solution, the herbicidal compounds are obtained in accordance with the following scheme:

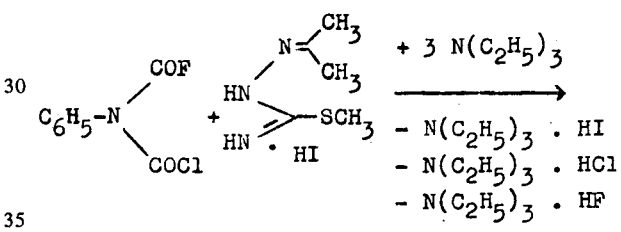

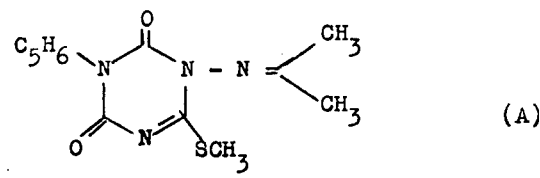
(A)

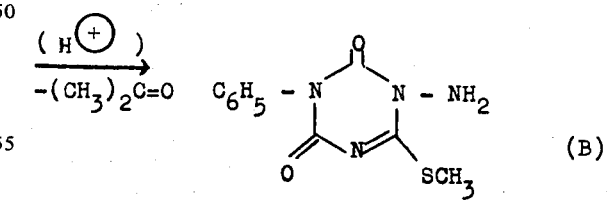
(B)

Application Example A 20 g (0.1 mol) of N-(fluorocarbonyl-chlorocarbonyl)-aniline were dissolved in 100 cc of benzene and the resulting solution was added dropwise with stirring to 27.3 g (0.1 mol) of acetone-S-methylisothiosemicarbazone hydriodide suspended in 100 cc of benzene. 30.3 g (0.3 mol) of triethylamine in 500 cc of benzene were then slowly added dropwise. The mixture was stirred for 1 hour and the precipitate was filtered off under suction. The precipitate was introduced into 100 cc of chloroform and 100 cc of water and extracted by shaking. The chloroform phase was separated off, dried over calcium chloride and concentrated by evaporation in vacuo together with the benzene filtrate. The residue was recrystallised from isopropanol, giving 20.6 g (72 %) of 1-phenyl-3-isopropylidene-amino-4-methylmercapto tetrahydro-1,3,5-triazin-2,6-dione corresponding to the formula

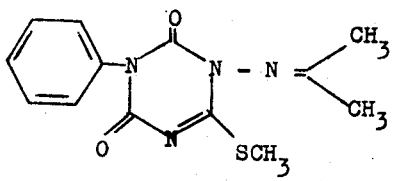

in the form of a pale yellow powder melting at 206° – 207°C.

Application Example B 29 g (0.1 mol) of 1-phenyl-3-isopropylidene-amino-4-methylmercapto-1,3,5-triazin-2,6-dione (prepared in accordance with Application Example A) were dissolved in 250 cc of ethanol and the resulting solution was heated for 5 hours to 50°C following the addition of a "spatula tip" of p-toluene sulphonic acid, a vacuum of around 200 mm Hg being applied. The product was concentrated by evaporation in vacuo and the residue recrystallised from ethanol, giving 24 g (96 %) of 1-phenyl-3-amino-4-methylmercapto tetrahydro-1,3,5-triazin-2,6-dione corresponding to the formula:

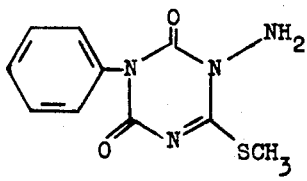

in the form of colourless needles melting at 205° to 208°C.

Pre-emergence Test

Solvent: 5 parts by weight of acetone
Emulsifier: 1 part by weight of alkylaryl polyglycol ether.

To prepare a suitable active-substance composition, 1 part by weight of active substance was mixed with the specified quantity of solvent, the specified quantity of emulsifier was added and the concentrate was diluted with water up to the required concentration.

Seeds of the test plants were sown in normal soil and watered with the active-substance preparation after 24 hours. The quantity of water applied per unit area is best kept constant. The concentration of active substance in the preparation is not important, the only important factor being the quantity of active substance applied per unit area. The degree of damage to the test plants was assessed after 3 weeks and characterised by marks of 0 to 5 which have the following meaning:

0 = no effect
1 = slight damage or growth retarded
2 = distinct damage or growth inhibited
3 = serious damage and defective development or only 50 % emergence
4 = plants partly destroyed after germination, or only 25 % emergence
5 = plants completely destroyed or no emergence.

The active substances, quantities applied and results are set out in the following Table:

| Active substance No. | A | A | B | B |
|---|---|---|---|---|
| Quantity of active substance applied kg/ha | 5 | 2.5 | 5 | 2.5 |
| Echinochloa | 5 | 4 | 5 | 4 |
| Chenopodium | 5 | 5 | 5 | 5 |
| Sinapis | 5 | 4 | 5 | 4 |
| Lolium | 5 | 5 | 5 | 5 |
| Stellaria | 5 | 5 | 5 | 5 |
| Galinsoga | 5 | 5 | 5 | 5 |
| Matricaria | 5 | 5 | 5 | 5 |
| Avena fatua | 5 | 5 | 4 | 3 |
| Cotton | 5 | 5 | 2 | 1 |
| Wheat | 3 | 3 | 3 | 3 |
| Buckwheat | 5 | 5 | 4–5 | 3 |
| Maize | 3 | 2 | 2 | 1 |

Further derivatives of tetrahydro-1,3,5-triazin-2,6-dione obtained in an analogous manner from the new compounds show similar herbicidal properties.

EXAMPLE 1

56 g (0.4 mol) of phenyl carbamic acid fluoride were dissolved in 200 ml of dry toluene. 50 g (0.5 mol) of phosgene were introduced into this solution at −10°C, followed by the gradual dropwise addition with stirring at −5 to +5°C of 32 g (0.4 mol) of dry pyridine. A colourless precipitate of pyridine hydrochloride was immediately formed. On completion of the dropwise addition, the mixture was allowed to come to room temperature while stirring, the precipitate was filtered off under suction and the solvent removed in a water-jet vacuum. The colourless, partly crystalline residue was either washed with petrol or distilled in a high vacuum. Fluorocarbonyl-chlorocarbonyl aniline corresponding to the formula

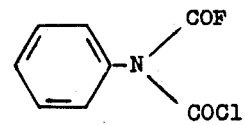

of m.p. 53° to 55°C was obtained in a yield of 48 g (60 %) at b.p. 80° to 85°C/0.1 Torr.

EXAMPLE 2

81 g (0.4 mol) of 3-chloro-4-methoxyphenyl carbamic acid fluoride were dissolved in 300 ml of dry toluene followed by the gradual dropwise addition at −5°C of 32 g (0.4 mol) of distilled pyridine. Approximately 50 g (0.5 mol) of phogene were introduced at a moderate rate into this clear solution while stirring at a temperature of −5° to 0°C. The mixture was allowed to come to room temperature over a period of 1 hour, and then stirred for approximately 2 hours at this temperature and the crystalline precipitate (hydrochloride) was filtered off under suction. The solvent was removed in a water-jet vacuum, leaving a colourless crystalline residue of 85 g (80 %) of 3-chloro-4-methoxy-N-fluorocarbonyl-N-chlorocarbonyl aniline corresponding to the formula

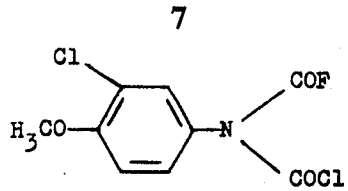

m.p. 124 to 127°C.

The 3-chloro-4-methoxyphenyl carbamic acid fluoride used for the reaction was obtained as follows:

20 to 25 cc of anhydrous hydrofluoric acid were introduced into a nickel vessel cooled to −5°C, diluted with approximately 80 cc of methylene chloride and 1 mol of 3-chloro-4-methoxyphenyl isocyanate was slowly added dropwise. The vessel was closed with a calcium chloride tube and its contents stirred for 2 hours at room temperature. The solvent was removed in vacuo with the excess hydrogen fluoride and the residue washed with petrol. The yield is quantitative. m.p.: 73° – 75 °C.

The other starting compounds (II) used for the process according to the invention can be similarly obtained.

The compounds set out in the following Table can be obtained in accordance with Examples 1 and 2.

| Example | Formula | Procedure according to Example No. | m.p.°C | Yield % |
| --- | --- | --- | --- | --- |
| 3 | H₃C—⌬—N(COF)(COCl) | 1 | 50 – 53 | 68 |
| 4 | Cl—⌬—N(COF)(COCl) | 1 | 88 – 91 | 75 |
| 5 | Cl,Cl—⌬—N(COF)(COCl) | 2 | 93 – 95 | 82 |
| 6 | F₃C—⌬—N(COF)(COCl) | 1 | 77 – 81 | 80 |
| 7 | F₃C—⌬—N(COF)(COCl) | 1 | 55 – 60 | 70 |
| 8 | F₃C,Cl—⌬—N(COF)(COCl) | 2 | 70 – 72 | 74 |
| 9 | Cl,F₃CO—⌬—N(COF)(COCl) | 2 | 74 – 78 | 81 |
| 10 | Cl,H₃C—⌬—N(COF)(COCl) | 2 | 56 – 60 | 83 |
| 11 | Cl,H₃CS—⌬—N(COF)(COCl) | 2 | 65 – 69 | 44 |
| 12 | Cl,F—⌬—N(COF)(COCl) | 1 | 83 – 85 | 78 |
| 13 | O₂N—⌬—N(COF)(COCl) | 2 | 87 – 90 | 52 |
| 14 | NC—⌬—N(COF)(COCl) | 2 | 102 – 105 | 47 |
| 15 | H₃CO₂S—⌬—N(COF)(COCl) | 2 | 75 (decomp.) | 38 |

EXAMPLE 16

28 g (0.2 mol) of phenyl carbamic acid fluoride were dissolved in 100 ml of dry toluene, followed by the gradual dropwise addition at −5°C to 0°C of 16 g (0.2 mol) of pyridine. 27 g (0.21 mol) of oxalyl chloride were slowly added dropwise to this solution with thorough stirring at −10°C to +5°C. Stirring was then continued for another 30 minutes at +5°C, and the mixture was allowed to come slowly to room temperature. The precipitate was filtered off and the solvent was removed in vacuo, leaving 19.5 g (46 % of the theoretical) of the compound

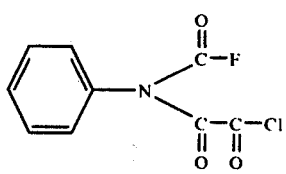

which melts at 111° to 115°C after recrystallisation from carbon tetrachloride or petrol.

What is claimed is:

1. Process for preparing bis-halogen carbonyl anilines having the formula

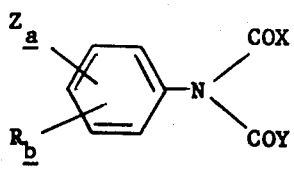

wherein
X is fluorine or chlorine,
Y is fluorine, chlorine, fluorocarbonyl, or chlorocarbonyl,
Z is halogen, nitro, cyano, lower alkyl sulfonyl or carbalkoxy
R is lower alkyl, alkoxy, thioalkyl, phenyl, naphthyl, lower perhalogen alkyl, perhalogen alkoxy or perhalogen alkylthio,
$a$ and $b$ represent a number from 0 to 5, with the proviso that $a$ plus $b$ is at the most 5,
which comprises reacting an aryl carbamic acid fluoride having the formula

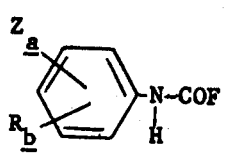

wherein
Z, R, $a$, $b$ are as defined above with an acylating agent having the formula

wherein

X and Y are as defined above in the presence of a tertiary amine at a temperature in the range of from −20 to +40°C.

2. Process of claim 1 wherein from 1 to 1.5 mols of the acylating agent and 1 mol of tertiary amine are used per mol of aryl carbamic acid fluoride.

3. Process of claim 1 wherein the reaction is carried out at a temperature of from −10 to +10°C.

4. Process of claim 1 wherein the acylating agent is phosgene or oxayl chloride.

5. Process for preparing bis-halogen carbonyl anilines having the formula

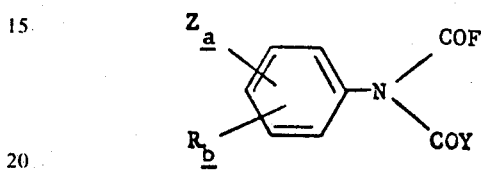

wherein
Y is chlorine, or chlorocarbonyl,
Z is halogen, nitro, cyano, lower alkyl sulfonyl or carbalkoxy
R is lower alkyl, alkoxy, thioalkyl, phenyl, naphthyl, lower perhalogen alkyl, perhalogen alkoxy or perhalogen alkylthio,
$a$ and $b$ represent a number from 0 to 5, with the proviso that $a$ plus $b$ is at the most 5,
which comprises reacting an aryl carbamic acid fluoride having the formula

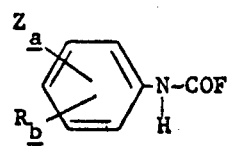

wherein
Z, R, $a$, $b$ are as defined above with an acylating agent of the group consisting of phosgene and oxadyl chloride in the presence of a tertiary amine at a temperature in the range of from −20 to +40°C.

6. Bis-halogen carbonyl anilines having the formula

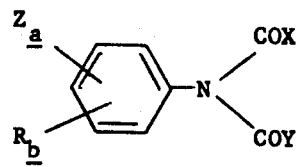

wherein
X is fluorine or chlorine,
Y is fluorocarbonyl or chlorocarbonyl and, when X is fluorine, Y can be chlorine, and when X is chlorine, Y can be fluorine,
Z is halogen, nitro, lower alkyl sulfonyl or
R is lower alkyl, alkoxy, thioalkyl, phenyl, naphthyl, and lower perhalogen alkyl, perhalogen alkoxy and perhalogen alkylthio,
$a$ and $b$ represent the numbers 0 to 5, with the proviso that $a$ plus $b$ is at most 5.

7. Compounds of claim 6 selected from the group of

4trifluoromethyl-N(chlorocarbonyl-fluorocarbonyl)-aniline,
3-Trifluoromethyl-N(chlorocarbonyl-fluorocarbonyl)-aniline,
3-Trifluoromethyl-4-chloro-N(chlorocarbonyl-fluorocarbonyl)-aniline.
3-Chloro-4-trifluoromethoxy-N(chlorocarbonyl-fluorocarbonyl)-aniline,
3-Chloro-4-methyl-N(chlorocarbonyl-fluorocarbonyl)-aniline,
3-Chloro-4-thiomethyl-N(chlorocarbonyl-fluorocarbonyl)-aniline,
3-Chloro-4-fluoro-N(chlorocarbonyl-fluorocarbonyl)-aniline,
4-Methylsulfonyl-N(chlorocarbonyl-fluorocarbonyl)-aniline,
Phenyl-N(chlorocarbonyl-fluorocarbonyl)-aniline,
3-Chloro-4-methoxy-N(chlorocarbonyl-fluorocarbonyl)-aniline,
4-Methyl-N(chlorocarbonyl-fluorocarbonyl)-aniline,
4-Chloro-N(chlorocarbonyl-fluorocarbonyl)-aniline,
3,4-Dichloro-N(chlorocarbonyl-fluorocarbonyl)-anile and
3-Nitro-N(chlorocarbonyl-fluorocarbonyl)-aniline.

8. Phenyl-N(chlorocarbonyl-fluorocarbonyl)-aniline.

* * * * *